(12) United States Patent
Thomas et al.

(10) Patent No.: US 10,813,693 B2
(45) Date of Patent: Oct. 27, 2020

(54) MICROWAVE ABLATION APPLICATORS

(71) Applicant: Gyrus Medical Limited, Cardiff (GB)

(72) Inventors: Tudor Thomas, Cardiff (GB); David Nicholas Williams, Caerphilly (GB); Lewis Jones, Cardiff (GB)

(73) Assignee: Gyrus Medical Limited, Cardiff (GB)

( * ) Notice: Subject to any disclaimer, the term of this patent is extended or adjusted under 35 U.S.C. 154(b) by 164 days.

(21) Appl. No.: 15/870,821

(22) Filed: Jan. 12, 2018

(65) Prior Publication Data

US 2019/0099219 A1    Apr. 4, 2019

(30) Foreign Application Priority Data

Feb. 10, 2017 (GB) .................................. 1702241.9

(51) Int. Cl.
*A61B 18/18* (2006.01)
*A61B 18/00* (2006.01)

(52) U.S. Cl.
CPC ............ *A61B 18/1815* (2013.01); *A61B 2018/00083* (2013.01); *A61B 2018/00577* (2013.01); *A61B 2018/1823* (2013.01); *A61B 2018/1838* (2013.01); *A61B 2018/1869* (2013.01); *A61B 2018/1892* (2013.01)

(58) Field of Classification Search
CPC ...... A61B 18/1815; A61B 2018/00083; A61B 2018/00577; A61B 2018/1823; A61B 2018/1838; A61B 2018/1869; A61B 18/18; A61B 2018/183; A61B 2018/1853; A61B 2018/1861; A61B 2018/1892; A61B 2018/00172
USPC ................... 606/32, 33; 607/101, 154, 156
See application file for complete search history.

(56) References Cited

U.S. PATENT DOCUMENTS

| 5,931,807 | A  | * | 8/1999 | McClure | ............... | A61B 18/18 604/27 |
| 7,128,739 | B2 | * | 10/2006 | Prakash | ............... | A61B 18/18 606/33 |
| 8,715,310 | B2 | * | 5/2014 | Pepper | ............... | A61M 25/10 156/189 |
| 2011/0077635 | A1 | * | 3/2011 | Bonn | .................. | H01Q 9/16 606/33 |
| 2011/0208184 | A1 | * | 8/2011 | Brannan | ............ | A61B 18/1815 606/41 |

OTHER PUBLICATIONS

Powys, Colin, "UK Search Report", prepared for application No. 1702241.9, Jun. 22, 2017, 6 pages.

* cited by examiner

*Primary Examiner* — Thomas A Guiliani
(74) *Attorney, Agent, or Firm* — Winstead PC

(57) ABSTRACT

A shaft assembly for a microwave ablation applicator having a shaft assembly and an antenna assembly located within the shaft assembly is disclosed. The shaft assembly comprises an elongate shaft which extends from a first end to a second end thereof and an applicator tip mounted on the second end of the elongate shaft.

9 Claims, 8 Drawing Sheets

MICROWAVE ABLATION APPLICATORS

CROSS-REFERENCE TO RELATED APPLICATIONS

This patent application claims priority from, and incorporates by reference the entire disclosure of, UK Patent Application GB 1702241.9 filed on Oct. 2, 2017.

The present invention relates to microwave ablation applicators, and, in particular, to shaft assemblies for such applicators.

BACKGROUND OF THE INVENTION

In the treatment of tumours, for example tumours caused by a disease such as cancer, it is known to use microwave ablation techniques to ablate the tumour. Such microwave ablation techniques typically ablate the targeted tissue by delivering a controlled amount of microwave energy into the tumour.

Minimally-Invasive techniques for delivering such microwave energy have been shown to be effective in the treatment of tumours. In a minimally-invasive technique, a microwave emitter is inserted directly into a point of treatment, either using a normal shaft orifice or via percutaneous insertion. Such minimally-invasive procedures and devices provide a means of treating tumours in patients who either cannot undergo other forms of treatment (e.g. radiotherapy, surgical resection, chemotherapy) or where ablation is preferred as a therapy.

The microwave emitter is provided in a microwave ablation applicator. One type of commonly used microwave ablation applicator has an elongate shaft assembly that houses an antenna assembly. The shaft assembly is provided by a shaft in the form of a thin walled cylinder which extends from a proximal end to a distal end thereof and defines an inner volume therein, and an applicator tip which is carried by, and closes, the distal end of the shaft. The applicator tip has a shape which is appropriate for insertion in to the tissue being treated, and which provides suitable electromagnetic properties. One particular exemplary antenna assembly includes a dipole antenna element located towards the distal end of the shaft in the inner volume of the shaft, adjacent the applicator tip. The antenna assembly also includes a coaxial conductor which extends along the inner volume of the shaft in order to connect the dipole antenna element to a source of microwave energy.

It is desirable for a microwave ablation applicator to be narrow and lightweight, but with high stiffness. For this reason, composite fibre-resin materials (also known as fibre reinforced plastics, (FRP) materials) have been considered as appropriate for the shaft. However, some fibre reinforced plastics materials result in undesirably thick side walls for the shaft leading to an undesirably large overall outer diameter of the shaft. Conversely, a desirably narrow shaft of the same material would result in lower than required stiffness of the shaft. Carbon fibre reinforced plastics (CFRP) materials enable the provision of a narrower side wall, and hence narrower shaft overall, due to the higher strength and stiffness of a CFRP material compared with other FRP materials. However, CFRP materials contain carbon fibres that are electrically conductive, and are, therefore, not suitable for attachment to an electrically conductive tip of the antenna assembly, since the conductivity of the carbon would prevent radiation of microwave energy from the applicator tip. In addition, conductive fibres may be heated by the microwave to unacceptably high temperatures.

It is, therefore, desirable to provide a shaft assembly that is able to address the drawbacks of the previously-considered designs.

SUMMARY OF THE INVENTION

According to a first aspect of the present invention, there is provided a shaft assembly for a microwave ablation applicator which includes a shaft assembly and an antenna assembly located within the shaft assembly, the shaft assembly comprising an elongate shaft which extends from a first end to a second end thereof, and which defines therein a hollow inner volume and a longitudinal axis of the antenna assembly; and an applicator tip mounted on the second end of the elongate shaft, wherein the elongate shaft comprises a first shaft portion which extends longitudinally from the first end of the shaft to an engagement region between the first and second ends of the elongate shaft, and a second portion which extends longitudinally from the engagement region to the second end of the elongate shaft, the first and second portions overlapping in the engagement region, and wherein the first shaft portion is of a carbon reinforced plastics material, and the second shaft portion is of a fibre reinforced plastics material having fibres which are non-electrically conductive.

In one example, the first and second shaft portions define respective first and second series of spaced apart elements which extend longitudinally, the first and second series of element interengaging with one another circumferentially around the shaft portions, such that the elements of the first and second series alternate circumferentially around the shaft in the engagement region.

In one example, the first shaft portion has an outer edge region that extends longitudinally, and wherein the second shaft portion has an inner edge region that extends longitudinally, the first and second edge regions overlapping one another longitudinally, thereby defining the engagement region. In one such example, wherein the inner and outer edge regions extend substantially parallel to an outer surface of the shaft. In one other such example, the outer edge region narrows in a direction towards the second shaft portion, and wherein the inner edge region narrows in a direction towards the first shaft portion.

In one example, the first shaft portion has an inner edge region that extends longitudinally, and wherein the second shaft portion has an outer edge region that extends longitudinally, the first and second edge regions overlapping one another longitudinally, thereby defining the engagement region. In one such example, the inner and outer edge regions extend substantially parallel to an outer surface of the shaft. In one other such example, the inner edge region narrows in a direction towards the second shaft portion, and wherein the outer edge region narrows in a direction towards the first shaft portion.

In one example, the applicator tip of the shaft assembly defines an annular slot with which the second end of the elongate shaft engages, and at least a part of the shaft is of a fibre reinforced plastics material having a plurality of elongate fibres bound in a plastics material, at least some of the fibres extending into the annular slot of the applicator tip, and extending at least partially circumferentially around the annular slot of the applicator tip.

In one example, at least some of the fibres extend along the elongate shaft substantially parallel to the longitudinal axis of the antenna assembly, those fibres extending into and at least partially around the annular slot in the applicator tip.

In such an example, at least some of the fibres may extend substantially circumferentially fully around the annular slot in the applicator tip.

In one example, substantially all of the fibres may extend into the annular slot.

In such an example, substantially all of the fibres may extend substantially circumferentially fully around the annular slot in the applicator tip.

In one example, the applicator tip of the shaft assembly defines an annular slot with which the second end of the elongate shaft engages, and at least a part of the shaft is of a fibre reinforced plastics material having a plurality of elongate fibres bound in a plastics material, at least some of which fibres extend into the annular slot of the applicator tip, the applicator tip further comprising at least one elongate fibre extending circumferentially around the annular slot thereof, radially outside of the fibres of the shaft, thereby to retain the fibres of the shaft in the annular slot.

In one example, the fibre reinforced plastics material includes carbon fibres, and the applicator tip is of an electrically insulating material.

In one example, the applicator tip comprises a base portion which engages an internal surface of the shaft, an intermediate portion which extends from the base portion, and a distal portion that extends from the intermediate portion to an end tip of the applicator tip, the base portion, intermediate portion and distal portion of the applicator tip defining the annular slot between a distal surface of the base portion and a proximal surface of the distal portion, the annular slot extending circumferentially around an outer surface of the intermediate portion.

In such an example, the base portion, intermediate portion, and distal portion of the applicator tip are provided by a single contiguous component.

According to a second aspect of the present invention, there is provided a microwave ablation antenna assembly comprising a shaft assembly according to the first aspect of the present invention, and an antenna assembly including an elongate coaxial conductor for connection to a source of microwave energy, the coaxial conductor extending from the first end of the shaft of the shaft assembly towards the second end of the shaft through the inner volume, the coaxial conductor having an inner conductor, a dielectric layer arranged radially outwardly of the inner conductor and extending along the inner conductor, and an outer conductor arrange radially outwardly of the dielectric layer and extending along the dielectric layer, the inner conductor defining a signal feed-point of the coaxial conductor at a distal end thereof towards the second end of the body, and a dipole tip portion which extends from the feed point of the coaxial conductor assembly towards the applicator tip of the shaft assembly, and which is electrically connected with the inner conductor of the coaxial conductor assembly.

DETAILED DESCRIPTION OF THE PREFERRED EMBODIMENTS

Figure 1:
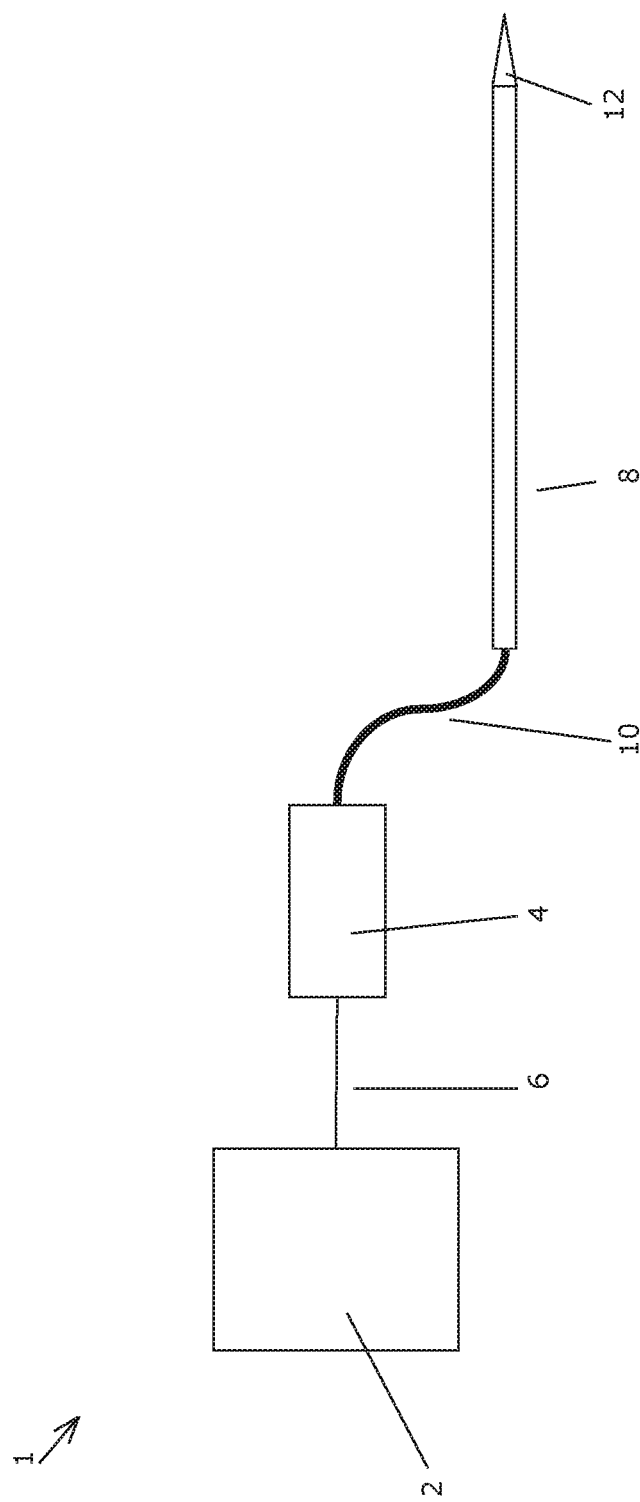
FIG. 1 is a schematic block diagram of a microwave ablation system.

FIG. 1 is a schematic diagram illustrating a microwave ablation system 1 comprising a controller unit 2, and a microwave power generator 4 which is connected to the controller via a control connection 6. An ablation applicator 8 is connected to the microwave power generator 4 via a power connection 10. The ablation applicator 8 includes a shaft assembly having a shaft which carries an applicator tip 12 which aids insertion of the ablation applicator 8 into the tissue being treated, and enables a desired output pattern of microwave energy from the ablation applicator 8.

The controller unit 2 is operable to control the power generator 4 to supply the correct magnitude and frequency of microwave energy to the ablation applicator 8. Different control schemes are known in the art, and will not be described here for the sake of clarity. The present invention is concerned with the design of the ablation applicator 8, and such an as ablation applicator 8 may be used with any appropriate control scheme and control hardware.

Figure 2:
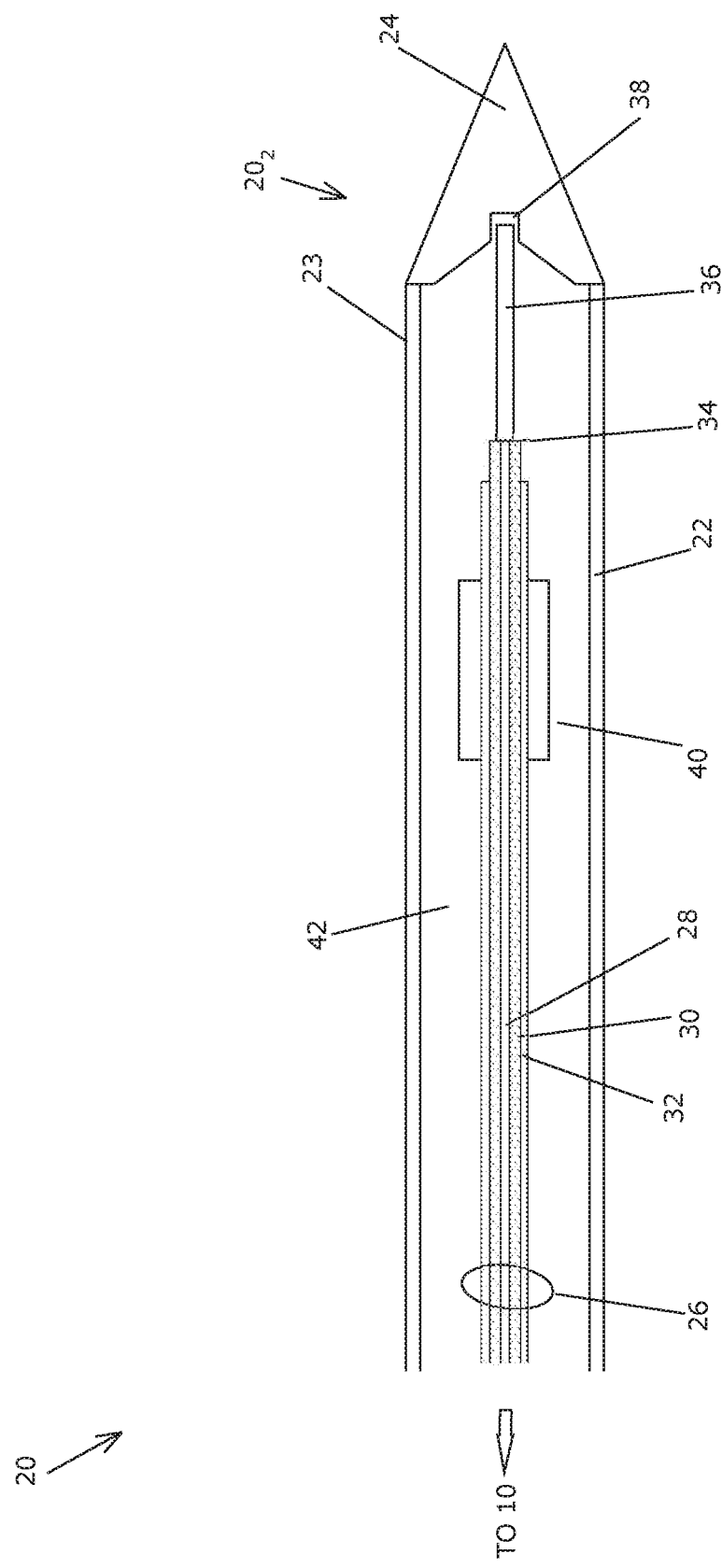
FIG. 2 is a cross sectional side view of part of a microwave ablation applicator.

FIG. 2 is a cross-sectional view of part of an ablation applicator 20 which comprises a shaft assembly and an antenna assembly. The shaft assembly includes a shaft 22, preferably cylindrical in form, which extends from a first (proximal) end $20_1$ to a second (distal) end $20_2$, and defines a longitudinal axis of the assembly and applicator. The second (distal) end $20_2$ of the shaft carries an applicator tip 24 for insertion into the tissue being treated. The shaft 22 defines an inner volume, in which most of the other components of the applicator are housed. The shaft 22 provides the applicator with the necessary rigidity for insertion into the tissue being treated. The shaft 22 is of a substantially rigid composite material, and is typically 1.5 to 3 mm in diameter.

The shaft assembly includes an applicator tip 24 which is attached to the second end $20_2$ of the shaft 22, so as to close off the inner volume at the second end. The applicator tip 24 is preferably a faceted trocar and has a relatively sharp distal end point. The applicator tip 24 is designed to be suitable for insertion into the tissue being treated, and partly to affect the transmission pattern for microwave energy into that tissue. The tip 24 also forms a water tight seal to the internal volume of the shaft 22.

The antenna assembly comprises a coaxial conductor 26 which extends along the inner volume of the shaft 22 from the first end $20_1$ towards the second end $20_2$. The coaxial conductor 26 is connectable, at a proximal end thereof, to the microwave energy generator 4 of FIG. 1. The coaxial conductor 26 comprises an inner conductor 28 of an electrically conductive material such as copper. Surrounding the inner conductor 28 is a dielectric layer 30 which extends along the inner conductor 28, radially outwardly thereof. The dielectric layer 30 is of any appropriate dielectric material. Surrounding the dielectric layer 30, is an outer conductor 32, which is of an electrically conductive material such as copper. The outer conductor 32 extends along an outer surface of the dielectric layer 30, radially outwards thereof. Typically, the inner conductor 28 is a wire having a circular cross section, such that the dielectric layer 30 is a cylinder of dielectric material surrounding an outer surface of the inner conductor 28. The outer conductor 32 is then formed by a cylinder of electrically conductive material surrounding an outer surface of the dielectric layer 30.

The dielectric layer 30 extends along the complete length of the inner conductor 28 to the distal end thereof. The outer conductor 32 stops short of the distal end of the inner conductor 28 and dielectric layer 30, and so is spaced apart longitudinally from that end point. The distal end of the coaxial conductor thereby defines a signal feed-point 34.

A dipole antenna element 36 extends longitudinally from the distal end (i.e. from the signal feedpoint 34) of the coaxial conductor 36 into a reception recess 38 in the applicator tip 24. The dipole antenna element 36 is connected to receive microwave energy from a microwave energy source by the coaxial conductor 26. The dipole antenna element 36 is arranged to emit microwave energy in a predetermined output pattern.

The reception recess 38 of the applicator tip 24 is located centrally with respect to the longitudinal axis of the assembly within the applicator tip 24. The reception recess 38 is designed so as to locate centrally the dipole tip portion 36 in the tip 24. The tip material is chosen for it mechanical and electrical properties, which have to be considered in the design.

A dielectric fluid may be provided within the inner volume of the shaft 20 in order to provide a dielectric element in the microwave design and also provide a cooling fluid for the antenna assembly. This fluid may be isotonic saline or deionised water.

In the example shown in FIG. 2, an electromagnetic choke assembly 40 is located within the shaft 22, around the coaxial conductor 26, spaced apart from the distal end of the coaxial conductor 26. It will be readily understood that the choke assembly is optional, depending on the design requirements of the assembly. The choke assembly 40 comprises a choke dielectric element 42 which extends around a portion of the outer conductor 32. In the case when the coaxial conductor 26 has a circular cross section, the choke dielectric element 42 is in the form of a cylinder of dielectric material surrounding an outer surface of the outer conductor 32 of the coaxial conductor 26. The choke dielectric has a proximal end towards the first end $20_1$ of the shaft 22 and a distal end towards the second end $20_2$ of the shaft 22. The length of the choke dielectric element 42 along the coaxial conductor 26 is determined by the desired electromagnetic/electrical characteristics of the choke assembly 40.

Figure 3:
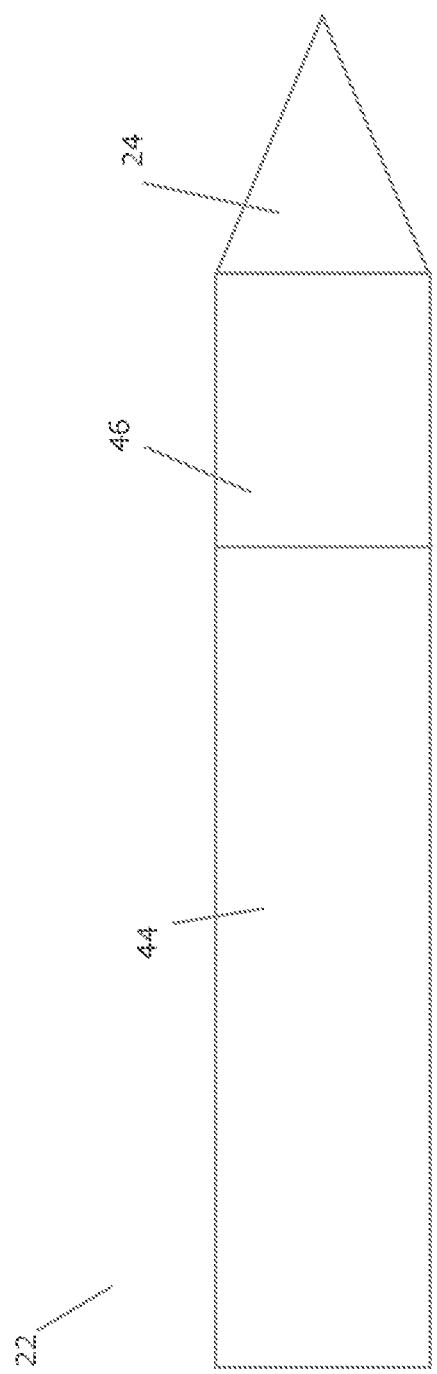
FIG. 3, FIG. 4, FIG. 5, FIG. 6, FIG. 7 and FIG. 8 are respective views of microwave ablation applicators embodying aspects of the present invention, and including a shaft assembly embodying other aspects of the present invention.

FIG. 3 illustrates a side view of a distal part of a shaft assembly embodying one aspect of the present invention. The shaft assembly comprises an elongate shaft 22 which carries an applicator tip 24 at a distal end, in line with the structure described above.

In a shaft assembly embodying an aspect of the present invention, the shaft 22 comprises first and second shaft portions 50 and 52. The first shaft portion 50 forms a proximal portion of the shaft 22, and the second shaft portion 52 forms a distal portion of the shaft 22. The first shaft portion 50 extends from a proximal end of the shaft 22, to an engagement region at its distal end on which the second shaft portion 52 is attached. The second shaft portion 52 extends from the engagement region to the distal end of the shaft 22. The applicator tip 24 is mounted on the distal end of the second shaft portion 52.

In an embodiment of an aspect of the present invention, the first shaft portion 50 is of a carbon fibre reinforced plastics (CFRP) material, and the second shaft portion is of a fibre reinforced plastics material (FRP) in which the fibres are not electrically conductive. Such a construction allows the use of CFRP for the majority of the length of the shaft 22, and so enables the shaft 22 to have the desirable narrow side wall and outer diameter, and high level of stiffness. The use of non-electrically conductive fibres in the second shaft portion 52 means that a metallic or other electrically conductive applicator tip 24 may be used.

Figure 4:
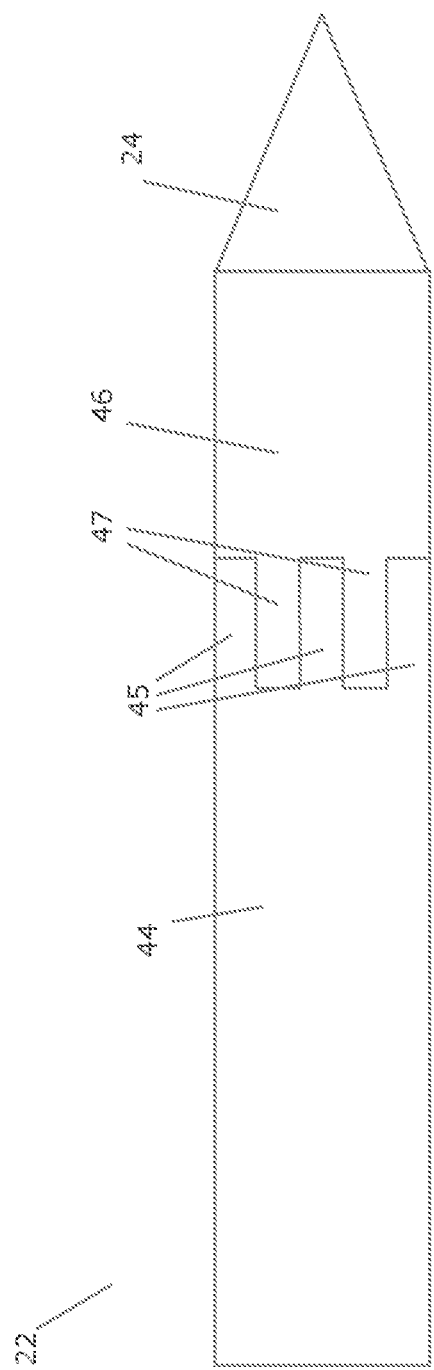
Figure 5:
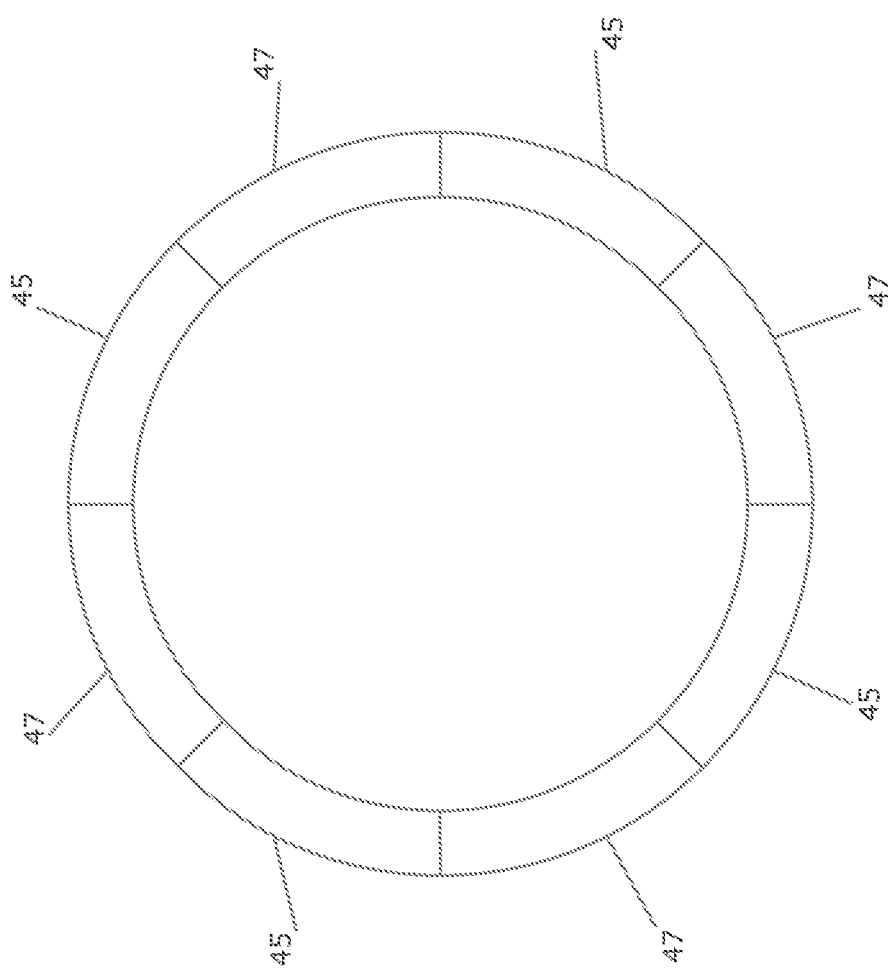

FIG. 4 illustrates a side view of the shaft assembly of FIG. 3, and shows a first technique for joining the first and second shaft portions 44 and 46. FIG. 5 illustrates a cross-sectional view of the joint between the first and second shaft portions 44 and 46. The technique shown in FIGS. 4 and 5 involves the distal end of the first shaft portion 44 being formed into a first series of spaced apart elements 45 that extend in a longitudinal direction from the distal end of the first shaft portion 44. The proximal end of the second shaft portion 46 being formed into a second series of spaced apart elements 47 that extend in a longitudinal direction from the proximal end of the second shaft portion 46. The first and second series of spaced apart elements 45 and 47 interengage with one another around the circumference of the shaft 22, such that the elements of the first and second series alternate circumferentially around the shaft.

Figure 6:
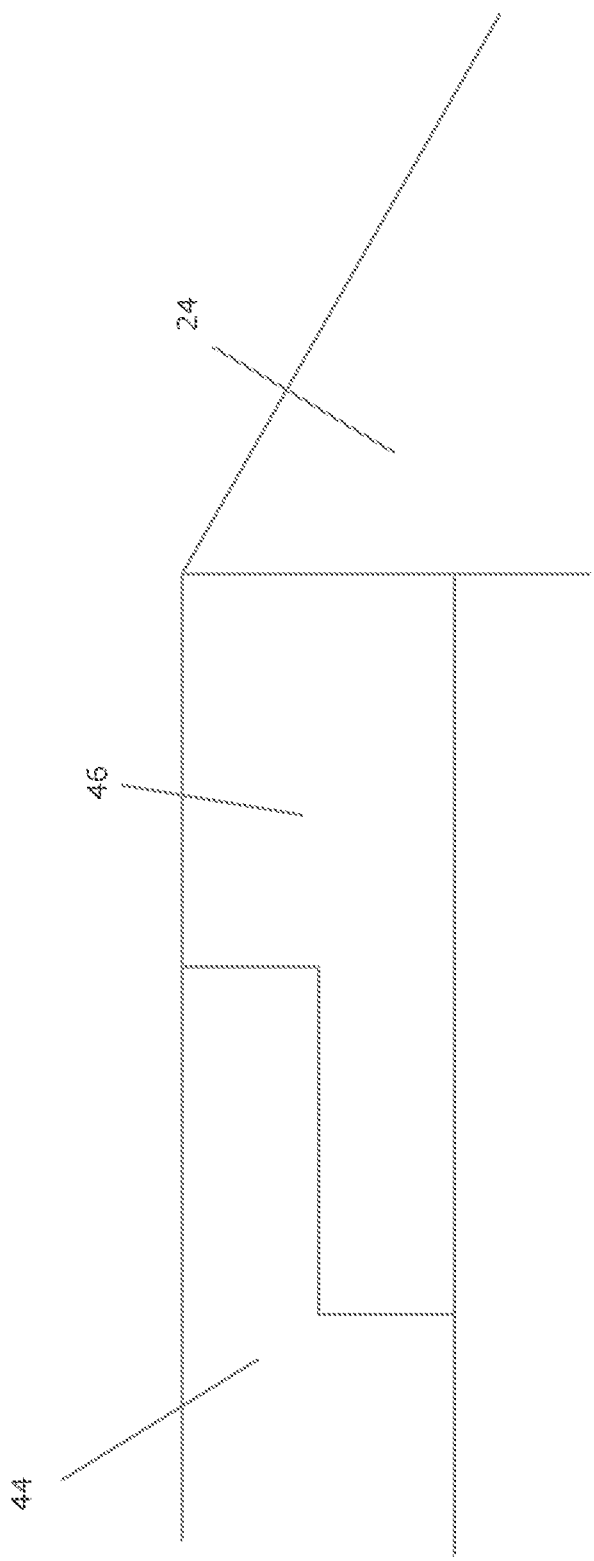

FIG. 6 is a partial cross-sectional side view of a second technique for attaching the second shaft portion 46 to the first shaft portion 44. In this technique, the first shaft portion 44 has an outer edge region 45 that overlaps an inner edge region 47 of the second shaft portion 46 in a longitudinal direction of the shaft 22. The outer edge region 45 and the inner edge region 47 thereby form a lap joint between the first and second shaft portions 44 and 46. It will be readily appreciated that the outer edge region 45 may be provided by the second edge portion 46, and that the inner edge region 47 may be provided by the first shaft portion 44.

Figure 7:
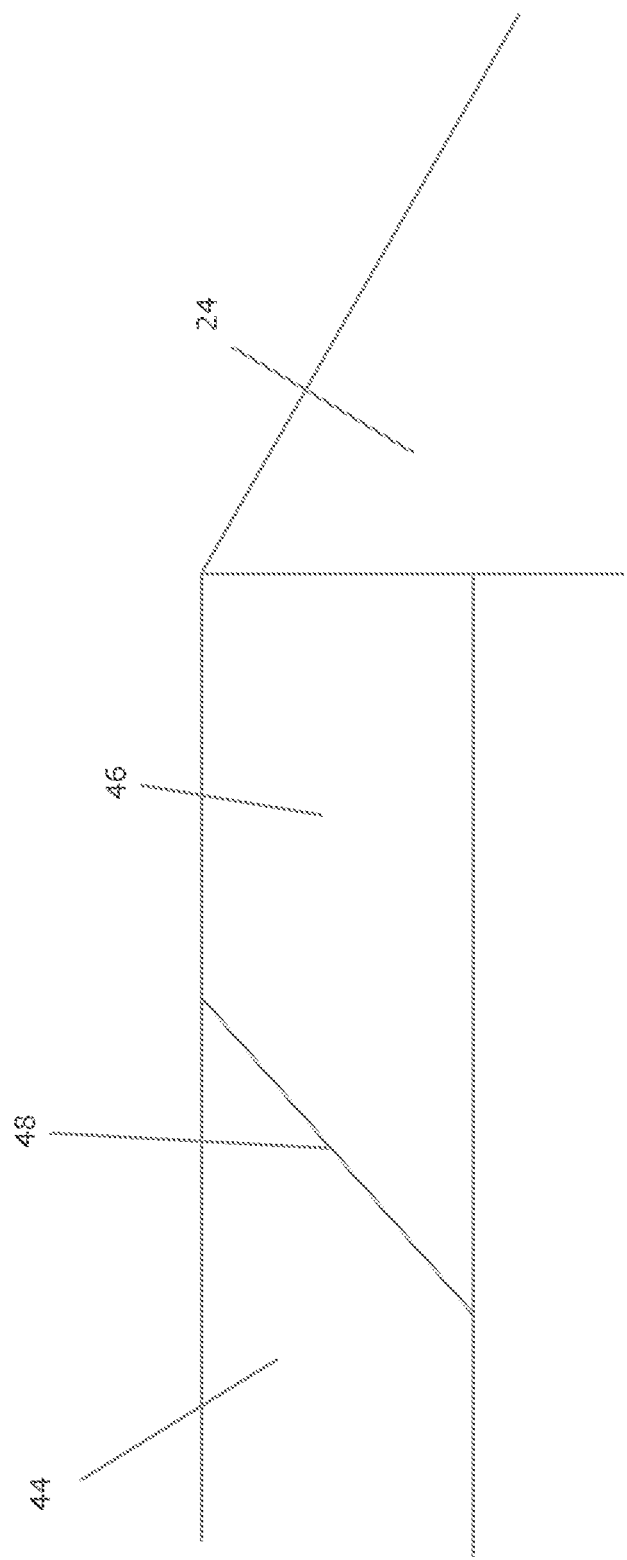

FIG. 7 is a partial cross-sectional side view of a third technique for attaching the second shaft portion 46 to the first shaft portion 44. In this technique, which is an adaptation of the second technique described above with reference to FIG. 6, the first shaft portion 44 narrows towards the distal end of the shaft to form a tapered outer edge region 45. The outer edge region 45 again overlaps the inner edge region 47 of the second shaft portion 46 in a longitudinal direction of the shaft 22. The inner edge region 47 narrows towards the proximal end of the second shaft portion 46. The outer edge region 45 and the inner edge region 47 thereby form a tapered lap joint between the first and second shaft portions 44 and 46. It will be readily appreciated that the outer edge region 45 may be provided by the second edge portion 46, and that the inner edge region 47 may be provided by the first shaft portion 44.

Figure 8:
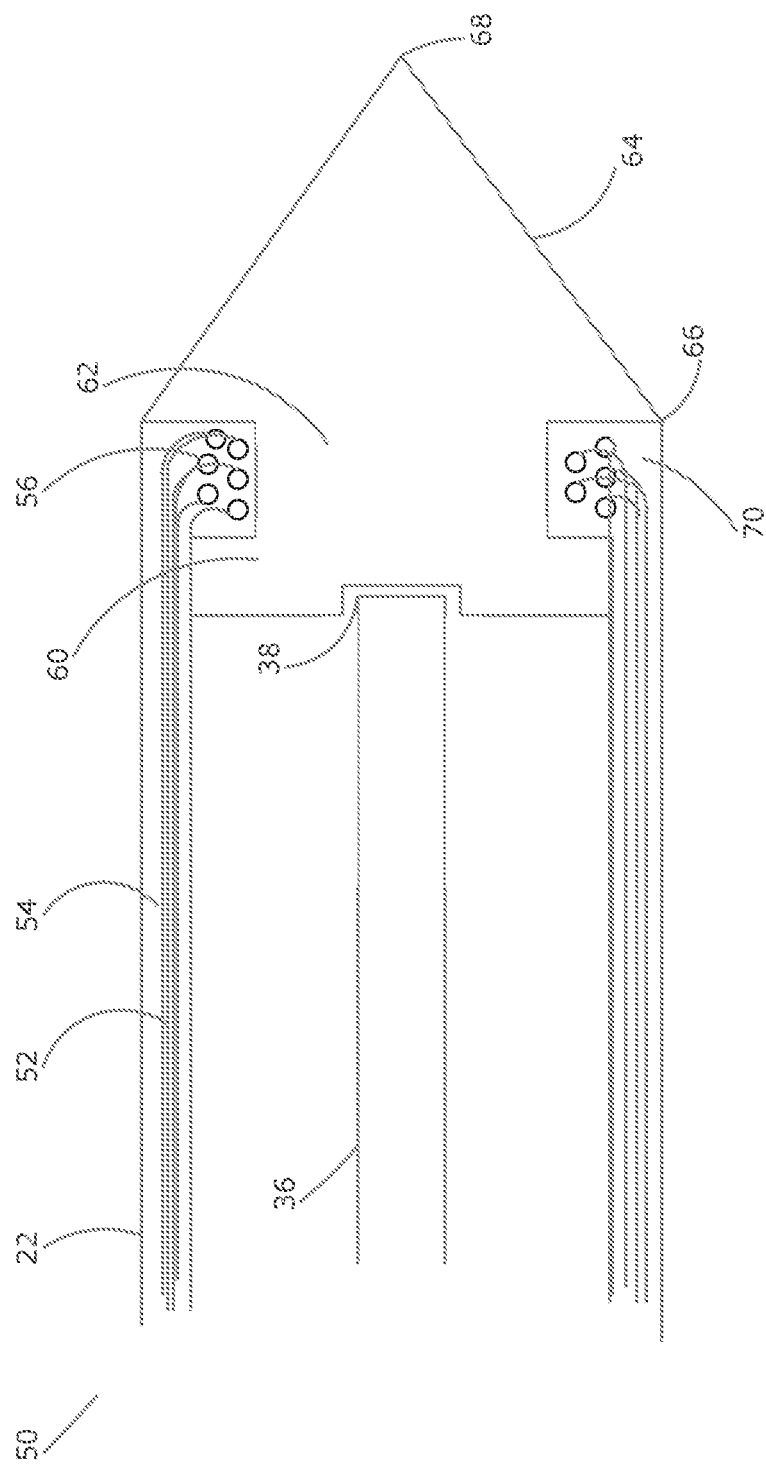

FIG. 8 illustrates, in side cross-sectional view, the distal end portion 50 of an ablation applicator that employs a technique for attachment of the applicator tip 24 to the shaft 22 suitable for use with a shaft assembly structure embodying an aspect of the present invention. The distal end portion 50 of FIG. 8 provides the second shaft portion 46 as described above with reference to an embodiment of the present invention. The dipole antenna element 36 extends through the distal end portion 50, to engage with the reception recess 38 of the applicator tip 24, as described with reference to FIG. 2 above.

In an embodiment of the present invention, the distal end portion 50 is of a fibre reinforced plastics material having no-electrically conductive fibres. Suitable fibre reinforced plastics materials include those using fibres of glass, or aramid, bound in a polymer material such as an epoxy, vinylester or polyester thermosetting plastics material. The distal end portion 50, therefore, includes a plurality of fibres 52 bound in plastics material 54.

The applicator tip 24 has an outer shape that matches cross section of the shaft 22, and is, therefore, preferably circular in cross section. The applicator tip 24 has a proximal base portion 60 which engages with the inner surface of the shaft 22, and which includes the reception recess 38. The applicator tip 24 has an intermediate portion 64 which extends from the base portion 60 towards a distal end of the tip 24. The intermediate portion 60 has an outer diameter smaller than that of the base portion 60. A distal portion 64 of the applicator tip 24 extends from the intermediate portion 62.

It will be readily appreciated that the base portion 60, intermediate portion 62 and distal portion 64 of the applicator tip 24 are preferably provided by a single contiguous component.

The distal portion 64 extends, and narrows, from an engagement portion 66 to a tip 68. The engagement portion 66 has an outer diameter substantially equal to that of the shaft 22, such that the shaft assembly has a substantially continuous outer profile, to aid insertion and retraction of the applicator. The base portion 60, intermediate portion 62 and distal portion 64 define an annular slot 70 therebetween. The annular slot 70 is defined between a distal surface of the base portion 60 and a proximal surface of the distal portion 64, and extending circumferentially around an outer surface of the intermediate portion 62.

The material of the shaft 22 extends into the annular slot 70 in order to secure the applicator tip 24 to the shaft 22. In one example, at least some of the fibres 52 have portions 56 thereof that extend into the annular slot 70 of the applicator tip 24, and extend at least partially circumferentially around the slot. The plastics material 54 extends into the annular slot 70.

In a preferred example, the fibres 52 of the shaft 22 extend individually substantially parallel to the longitudinal axis of the assembly to the applicator tip 24, such that the shaft is formed of a unidirectional fibre reinforced material. Each fibre 52 extends 56 into the annular slot 70 of the applicator tip 24. The fibres 52, 56 may extend fully, partially or multiple times circumferentially around the annular slot 70. The fibres 52, 56 are preferably looped around the intermediate portion 62 of the applicator tip 24 to provide a secure anchoring technique for the applicator tip 24.

In order to manufacture such an assembly, the fibres of the shaft 22 are looped around the applicator tip 24, in the form described above. The fibres are then laid up in an appropriate orientation in a mould for the shaft 22. Liquid resin is then introduced into the mould in order to form the desired shape. The resin extends into the annular slot 70, thereby surrounding the fibres 56 extending into the slot 70. The mould ins then evacuated of air, and the resin cured, in conventional manner. The resulting structure provides the elongate shaft 22, having an end closed by an applicator tip 24 securely fastened to the shaft 22.

The invention claimed is:

1. A shaft assembly for a microwave ablation applicator which includes a shaft assembly and an antenna assembly located within the shaft assembly, the shaft assembly comprising:
   an elongate shaft which extends from a first end to a second end thereof, and which defines therein a hollow inner volume and a longitudinal axis of the antenna assembly; and
   an applicator tip mounted on the second end of the elongate shaft,
   wherein the elongate shaft comprises a first shaft portion which extends longitudinally from the first end of the shaft to an engagement region between the first and second ends of the elongate shaft, and a second shaft portion which extends longitudinally from the engagement region to the second end of the elongate shaft, the first and second shaft portions overlapping in the engagement region,
   wherein the first shaft portion is of a carbon reinforced plastics material, and the second shaft portion is of a fibre reinforced plastics material having a plurality of elongate fibres which are non-electrically conductive, and
   wherein the applicator tip of the shaft assembly defines an annular slot with which the second end of the elongate shaft engages, and wherein at least some of the plurality of elongate fibres extend into the annular slot of the applicator tip, and extend at least partially circumferentially around the annular slot of the applicator tip.

2. A shaft for a microwave ablation applicator which includes a shaft assembly and an antenna assembly located within the shaft assembly, the shaft assembly comprising:
   an elongate shaft which extends from a first end to a second end thereof, and which defines therein a hollow inner volume and a longitudinal axis of the antenna assembly; and
   an applicator tip mounted on the second end of the elongate shaft,
   wherein the elongate shaft comprises a first shaft portion which extends longitudinally from the first end of the shaft to an engagement region between the first and second ends of the elongate shaft, and a second shaft portion which extends longitudinally from the engagement region to the second end of the elongate shaft, the first and second shaft portions overlapping in the engagement region,
   wherein the first shaft portion is of a carbon reinforced plastics material, and the second shaft portion is of a fibre reinforced plastics material having a plurality of elongate fibres which are non-electrically conductive, and
   wherein the applicator tip of the shaft assembly defines an annular slot with which the second end of the elongate shaft engages, and wherein at least some of the plurality of elongate fibres extend into the annular slot of the applicator tip, and extend at least partially circumferentially around the annular slot of the applicator tip, and wherein the at least some of the plurality of elongate fibres extend along the elongate shaft substantially parallel to the longitudinal axis of the antenna assembly.

3. A shaft for a microwave ablation applicator which includes a shaft assembly and an antenna assembly located within the shaft assembly, the shaft assembly comprising:
   an elongate shaft which extends from a first end to a second end thereof, and which defines therein a hollow inner volume and a longitudinal axis of the antenna assembly; and
   an applicator tip mounted on the second end of the elongate shaft,
   wherein the elongate shaft comprises a first shaft portion which extends longitudinally from the first end of the shaft to an engagement region between the first and second ends of the elongate shaft, and a second shaft portion which extends longitudinally from the engagement region to the second end of the elongate shaft, the first and second shaft portions overlapping in the engagement region,
   wherein the first shaft portion is of a carbon reinforced plastics material, and the second shaft portion is of a fibre reinforced plastics material having a plurality of elongate fibres which are non-electrically conductive, and the applicator tip of the shaft assembly defines an annular slot with which the second end of the elongate shaft engages, and wherein at least some of the plurality of elongate fibres extend into the annular slot of the applicator tip, and extend substantially circumferentially fully around the annular slot of the applicator tip, and wherein the at least some of the plurality of elongate fibres extend along the elongate shaft substantially parallel to the longitudinal axis of the antenna assembly.

4. A shaft for a microwave ablation applicator which includes a shaft assembly and an antenna assembly located within the shaft assembly, the shaft assembly comprising:

an elongate shaft which extends from a first end to a second end thereof, and which defines therein a hollow inner volume and a longitudinal axis of the antenna assembly; and an applicator tip mounted on the second end of the elongate shaft, wherein the elongate shaft comprises a first shaft portion which extends longitudinally from the first end of the shaft to an engagement region between the first and second ends of the elongate shaft, and a second shaft portion which extends longitudinally from the engagement region to the second end of the elongate shaft, the first and second shaft portions overlapping in the engagement region, wherein the first shaft portion is of a carbon reinforced plastics material, and the second shaft portion is of a fibre reinforced plastics material having a plurality of elongate fibres which are non-electrically conductive, and wherein the applicator tip of the shaft assembly defines an annular slot with which the second end of the elongate shaft engages, and wherein substantially all of the plurality of elongate fibres extend into the annular slot of the applicator tip, and extend along the elongate shaft substantially parallel to the longitudinal axis of the antenna assembly, and wherein at least some of the plurality of elongate fibres extend at least partially circumferentially around the annular slot of the applicator tip.

5. A shaft for a microwave ablation applicator which includes a shaft assembly and an antenna assembly located within the shaft assembly, the shaft assembly comprising:

an elongate shaft which extends from a first end to a second end thereof, and which defines therein a hollow inner volume and a longitudinal axis of the antenna assembly; and an applicator tip mounted on the second end of the elongate shaft, wherein the elongate shaft comprises a first shaft portion which extends longitudinally from the first end of the shaft to an engagement region between the first and second ends of the elongate shaft, and a second shaft portion which extends longitudinally from the engagement region to the second end of the elongate shaft, the first and second shaft portions overlapping in the engagement region, wherein the first shaft portion is of a carbon reinforced plastics material, and the second shaft portion is of a fibre reinforced plastics material having a plurality of elongate fibres which are non-electrically conductive, and wherein the applicator tip of the shaft assembly defines an annular slot with which the second end of the elongate shaft engages, and wherein substantially all of the plurality of elongate fibres extend into the annular slot of the applicator tip, and extend substantially circumferentially fully around the annular slot of the applicator tip, and wherein the plurality of elongate fibres extend along the elongate shaft substantially parallel to the longitudinal axis of the antenna assembly.

6. A shaft for a microwave ablation applicator which includes a shaft assembly and an antenna assembly located within the shaft assembly, the shaft assembly comprising:

an elongate shaft which extends from a first end to a second end thereof, and which defines therein a hollow inner volume and a longitudinal axis of the antenna assembly; and an applicator tip mounted on the second end of the elongate shaft, wherein the elongate shaft comprises a first shaft portion which extends longitudinally from the first end of the shaft to an engagement region between the first and second ends of the elongate shaft, and a second shaft portion which extends longitudinally from the engagement region to the second end of the elongate shaft, the first and second shaft portions overlapping in the engagement region, wherein the first shaft portion is of a carbon reinforced plastics material, and the second shaft portion is of a fibre reinforced plastics material having a plurality of elongate fibres which are non-electrically conductive, and wherein the applicator tip of the shaft assembly defines an annular slot with which the second end of the elongate shaft engages, and wherein at least some of the plurality of elongate fibres extend into the annular slot of the applicator tip, wherein at least one elongate fibre from the plurality of elongate fibres extends circumferentially around the annular slot thereof.

7. A shaft for a microwave ablation applicator which includes a shaft assembly and an antenna assembly located within the shaft assembly, the shaft assembly comprising:

an elongate shaft which extends from a first end to a second end thereof, and which defines therein a hollow inner volume and a longitudinal axis of the antenna assembly; and an applicator tip mounted on the second end of the elongate shaft, wherein the elongate shaft comprises a first shaft portion which extends longitudinally from the first end of the shaft to an engagement region between the first and second ends of the elongate shaft, and a second shaft portion which extends longitudinally from the engagement region to the second end of the elongate shaft, the first and second shaft portions overlapping in the engagement region, wherein the first shaft portion is of a carbon reinforced plastics material, and the second shaft portion is of a fibre reinforced plastics material having a plurality of elongate fibres which are non-electrically conductive, and wherein the applicator tip of the shaft assembly defines an annular slot with which the second end of the elongate shaft engages, and wherein at least some of the plurality of elongate fibres extend into the annular slot of the applicator tip, and extend at least partially circumferentially around the annular slot of the applicator tip, and wherein the plurality of elongate fibres comprise carbon fibres, and the applicator tip is of an electrically insulating material.

8. A shaft for a microwave ablation applicator which includes a shaft assembly and an antenna assembly located within the shaft assembly, the shaft assembly comprising:
an elongate shaft which extends from a first end to a second end thereof, and which defines therein a hollow inner volume and a longitudinal axis of the antenna assembly; and
an applicator tip mounted on the second end of the elongate shaft,
wherein the elongate shaft comprises a first shaft portion which extends longitudinally from the first end of the shaft to an engagement region between the first and second ends of the elongate shaft, and a second shaft portion which extends longitudinally from the engagement region to the second end of the elongate shaft, the first and second shaft portions overlapping in the engagement region,
wherein the first shaft portion is of a carbon reinforced plastics material, and the second shaft portion is of a fibre reinforced plastics material having a plurality of elongate fibres which are non-electrically conductive, and
wherein the applicator tip of the shaft assembly defines an annular slot with which the second end of the elongate shaft engages, and wherein at least some of the plurality of elongate fibres extend into the annular slot of the applicator tip, and extend at least partially circumferentially around the annular slot of the applicator tip, and wherein the applicator tip comprises a base portion which engages an internal surface of the elongate shaft, an intermediate portion which extends from the base portion, and a distal portion that extends from the intermediate portion to an end tip of the applicator tip, the base portion, intermediate portion and distal portion of the applicator tip defining the annular slot between a distal surface of the base portion and a proximal surface of the distal portion, the annular slot extending circumferentially around an outer surface of the intermediate portion.

9. A shaft for a microwave ablation applicator which includes a shaft assembly and an antenna assembly located within the shaft assembly, the shaft assembly comprising:
an elongate shaft which extends from a first end to a second end thereof, and which defines therein a hollow inner volume and a longitudinal axis of the antenna assembly; and
an applicator tip mounted on the second end of the elongate shaft,
wherein the elongate shaft comprises a first shaft portion which extends longitudinally from the first end of the shaft to an engagement region between the first and second ends of the elongate shaft, and a second shaft portion which extends longitudinally from the engagement region to the second end of the elongate shaft, the first and second shaft portions overlapping in the engagement region,
wherein the first shaft portion is of a carbon reinforced plastics material, and the second shaft portion is of a fibre reinforced plastics material having a plurality of elongate fibres which are non-electrically conductive, and
wherein the applicator tip of the shaft assembly defines an annular slot with which the second end of the elongate shaft engages, and wherein at least some of the plurality of elongate fibres extend into the annular slot of the applicator tip, and extend at least partially circumferentially around the annular slot of the applicator tip, and wherein the applicator tip comprises a base portion which engages an internal surface of the elongate shaft, an intermediate portion which extends from the base portion, and a distal portion that extends from the intermediate portion to an end tip of the applicator tip, the base portion, intermediate portion and distal portion of the applicator tip defining the annular slot between a distal surface of the base portion and a proximal surface of the distal portion, the annular slot extending circumferentially around an outer surface of the intermediate portion, and wherein the base portion, intermediate portion, and distal portion of the applicator tip are provided by a single contiguous component.

* * * * *